United States Patent [19]

Kleiner et al.

[11] Patent Number: 4,693,884

[45] Date of Patent: Sep. 15, 1987

[54] TECHNETIUM-99M TRIPHOSPHONATES AND TETRAPHOSPHONATES FOR THE SCINTIGRAPHIC VISUALIZATION OF RES-CONTAINING ORGANS AND LYMPH VESSELS, AND A PROCESS FOR THEIR PREPARATION

[75] Inventors: Hans-Jerg Kleiner, Kronberg/Taunus; Gerhard Kloss, Kelkheim; Michael Molter, Schwalbach; Alexander Schwarz, Flörsheim am Main; Horst-Dieter Thamm, Kelkheim, all of Fed. Rep. of Germany

[73] Assignee: Hoechst Aktiengesellschaft, Fed. Rep. of Germany

[21] Appl. No.: 540,173

[22] Filed: Oct. 7, 1983

[30] Foreign Application Priority Data

Oct. 9, 1982 [DE] Fed. Rep. of Germany ..... 32375735

[51] Int. Cl.$^4$ ..................... A61K 43/00; A61K 49/00; A61K 49/02
[52] U.S. Cl. ......................................... 424/1.1; 424/9; 534/14
[58] Field of Search ....................... 424/1.1, 9; 534/14

[56] References Cited

U.S. PATENT DOCUMENTS

| | | | |
|---|---|---|---|
| 3,740,418 | 6/1973 | Rajamani et al. | 424/1.1 |
| 3,976,762 | 8/1976 | Köhler et al. | 424/1.1 |
| 3,983,227 | 9/1976 | Tofe et al. | 424/1.1 |
| 4,027,005 | 5/1971 | Adler et al. | 424/1.1 |
| 4,058,593 | 11/1977 | Nora | 424/1.1 |
| 4,104,366 | 8/1978 | Schmidt-Dunker et al. | 424/1.1 |
| 4,115,541 | 9/1978 | Subramanian et al. | 424/1.1 |
| 4,133,872 | 6/1979 | Schmidt-Dunker et al. | 424/1.1 |
| 4,226,846 | 10/1980 | Saklad | 424/1.1 |
| 4,234,562 | 11/1980 | Tofe et al. | 424/1.1 |
| 4,272,503 | 6/1981 | Camin et al. | 424/1.1 |
| 4,291,012 | 9/1981 | Strecker et al. | 424/1.1 |
| 4,399,817 | 8/1983 | Benedict | 424/1.1 |
| 4,440,738 | 4/1984 | Fawzi et al. | 424/1.1 |
| 4,451,450 | 4/1984 | Subramanyam | 424/1.1 |
| 4,455,291 | 6/1984 | Tweedle | 424/1.1 |

FOREIGN PATENT DOCUMENTS 1541070 2/1979 United Kingdom ................. 424/1.1

OTHER PUBLICATIONS

Van Den Brand et al., Int. J. Appl. Radiat. Isot., 33 (1982) 917–28.

*Primary Examiner*—Christine M. Nucker
*Attorney, Agent, or Firm*—Finnegan, Henderson, Farabow, Garrett & Dunner

[57] ABSTRACT

A diagnostic agent for the visualization of RES-containing organs or of lymph vessels, containing $^{99m}Tc$ triphosphonates or tetraphosphonates in physiologic saline, and a process for their preparation.

2 Claims, No Drawings

TECHNETIUM-99M TRIPHOSPHONATES AND TETRAPHOSPHONATES FOR THE SCINTIGRAPHIC VISUALIZATION OF RES-CONTAINING ORGANS AND LYMPH VESSELS, AND A PROCESS FOR THEIR PREPARATION

The present invention relates to new products for the scintigraphic visualization of RES-containing organs, especially the liver and spleen, and the lymph vessels.

Because of its favorable physical properties (no corpuscular radiation, gamma energy 140 keV and half-life 6 hours) and the associated low exposure to radiation, as well as because it is straightforward to obtain using nuclide generators, technetium-99m has gained widespread acceptance in recent years for diagnostic methods in nuclear medicine.

The technetium-99m obtained from generators of this type is initially in the form of the pertechnetate and this is suitable, for example, for thyroid and brain scintigraphy. Products have been developed for diagnostic methods relating to other organs, which products can be readily labeled with technetium-99m and which accumulate in particular organs with high selectivity. Thus, for example, the skeleton can be visualized using labeled phosphonic acids, or the kidneys can be visualized using labeled hydrophilic complexes, such as, for example, with ethylenediaminetetraacetic acid.

In general, in order to label organ-specific "transport substances" with technetium-99m, it is necessary to convert the pertechnetate ($TcO_4^-$), which is the form initially obtained and is very unreactive, into a lower and more reactive oxidation state. In this reduced form, technetium becomes reactive and forms comparatively stable compounds with the appropriate "transport substances".

The reduction of $TcO_4^-$ can be carried out by chemical reducing agents or electrolytically; tin(II) salts are most frequently used for the reduction.

The reduction with tin(II) has the advantage that the reducing agent and the organ-specific transport substance, generally in a freeze-dried form, can be stored together in one injection vial so that it is only necessary for the preparation of the product ready for use in the clinic to add a solution having the desired $^{99m}Tc$ activity.

As a rule, colloids labeled with technetium-99m which, after intravenous administration, are removed by the reticuloendothelial system (RES) from the blood in a relatively short time are used for static liver scintigraphy. Since RES is localized not only in the liver but also in the spleen and red bone marrow, it is obvious that part of the radioactivity will also accumulate in these tissues.

The following are examples of known products for visualizing the RES using $^{99m}TC$-labeled colloids:

1. Technetium-99m/sulfur colloid
2. Technetium-99m/tin hydroxide colloid
3. Technetium-99m/tin/phenazone colloid
4. Technetium-99m/albumin millimicrospheres
5. Technetium-99m phytate All these products have certain disadvantages, such as, for example:

Technetium-99m/sulfur colloid is a product which is very useful in respect of its diagnostic properties, but a relatively elaborate process is necessary to prepare it: the solution containing technetium-99m must first be acidified, thiosulfate is added, then the mixture is boiled and finally neutralized. This is associated with a high exposure of the hospital staff to radiation.

Technetium-99m/tin hydroxide colloid is generally prepared by dissolving a tin(II) salt, for example $SnCl_2$ or $SnF_2$, by addition of the solution containing the $^{99m}Tc$-pertechnetate, and at the pH of this solution, which is between 4.5 and 7 as a rule, tin hydroxide is formed. At the same time, the technetium which is reduced by the tin(II) also precipitates. The size of the colloidal particles produced thereby depends on many factors, such as, for example, the temperature, the rate of injection of the pertechnetate solution into the labeling container and the eluate volume. Moreover, over the course of time, the particles aggregate and this, in certain circumstances, can lead to unintended visualization of the lungs.

Technetium-99m/tin/phenazone colloid is in fact labeled as a preformed colloid but again, under certain circumstances, aggregation of the particles can occur and this occasionally causes undesired visualization of the lungs.

Technetium-99m/albumin millimicrospheres comprise denatured albumin particles which contain a certain amount of Sn(II) to reduce the pertechnetate. The disadvantages of this product are, on the one hand, that the preparation is very elaborate and slight deviations from the optimal conditions for preparation lead to changes in the particle size and thus, in certain circumstances, to undesired organic distribution. On the other hand, as with all products containing albumin particles, more or less strong adhesion to the walls of syringes, cannulas and containers occur, depending on the materials used in the containers and injection syringes, so that a certain proportion of the radioactivity is retained.

Technetium-99m phytate has a mechanism of action which is quite different from the products described hitherto, since in this case, in contrast to the latter, no colloid is present in the solution ready for administration. The colloid is only formed in the blood after i.v. injection, probably by formation of the very sparingly soluble Ca salt. The principal disadvantage of this product is that the accumulation of activity in the RES is low compared with the products mentioned above.

The object of the present invention is to provide a diagnostic agent for the visualization of RES-containing organs and the lymph vessels.

The invention relates to a process for the preparation of a diagnostic agent for the visualization of RES-containing organs, especially the liver, and the lymph vessels, which comprises mixing one or more compounds from the group comprising 2,4,4-triphosphonobutyric acid or ethane-1,1,2,2-tetraphosphonic acid or propane-1,1,3,3-tetraphosphonic acid or butane-1,1,4,4-tetraphosphonic acid or suitable salts thereof, in aqueous solution, with a tin(II) salt, adjusting the pH of the solution to a value between 2 and 10, preparing individual small portions, optionally freezedrying the mixture, and then adding, depending on the purpose for which it is to be used, 3.7–3700 MBq (0.1–100 mCi) of technetium-99m pertechnetate in physiologic saline.

It is possible to use phosphoric acid derivatives, particularly organic phosphonic acid derivatives, for bone scintigraphy. Many compounds have been investigated in the search for derivatives suitable as a technetium-99m diagnostic agent for bone. Surprisingly, of the phosphoric acid derivatives investigated, 2,4,4-triphosphonobutyric acid (TPB), ethane-1,1,2,2-tetraphosphonic acid (ETP), propane-1,1,3,3-tetraphosphonic acid (PTP) and butane-1,1,4,4-tetraphosphonic acid (BTP) accumulated virtually not at all in bone, but very preferentially accumulated in the liver.

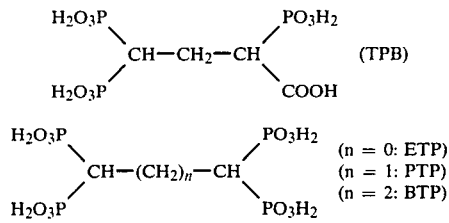

TPB is prepared from the corresponding heptaalkyl ester by hydrolysis. The heptaalkyl ester is obtained by base-catalyzed addition of alkyl 1-dialkoxyphosphonoacrylate to tetraalkyl methylenediphosphonate.

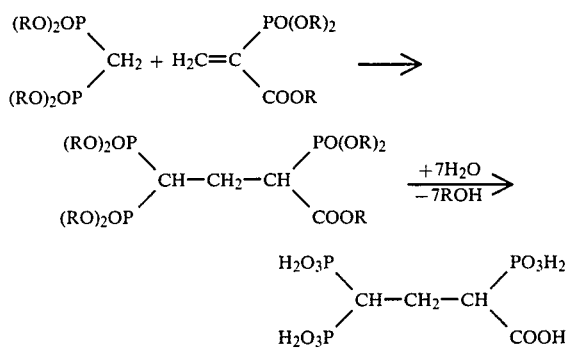

The other alkanetetraphosphonic acids are prepared by known processes.

The mechanism of accumulation of these products in the liver is most probably similar to that of the phytate, but in the case of the phytate the accumulations in the RES are lower and the accumulation in bone is higher.

A reasonable amount in one container (a labeling) unit) suitable for use in humans is 0.1–200 mg, preferably 2–50 mg, of the appropriate triphosphonic or tetraphosphonic acid. The concentration of tin(II) should be at a molar ratio of 1:10 to 1:500, preferably between 1:50 and 1:150, relative to the particular triphosphonic or tetraphosphonic acid.

$SnF_2$, $SnSO_4$, SnO, Sn acetate, Sn oxalate, Sn-tartrate or another salt can be used as the tin(II) salts; the chloride is preferred, especially $SnCl_2.2H_2O$.

For the preparation of the labeling unit, it is an advantage when the appropriate triphosphonic or tetraphosphonic acid or a suitable salt thereof is dissolved in water, the pH of the solution is adjusted to 5–7 with sodium hydroxide solution or hydrochloric acid, the appropriate tin(II) salt is added in a solution which has been slightly acidified with hydrochloric acid, the solution is adjusted to the desired volume with water, the pH is again adjusted to 5–7, and then the solution is divided in small individual portions optionally freeze-dried and finally covered with protective gas, such as, for example, nitrogen.

The invention also relates to a diagnostic agent for the visualization of RES-containing organs and the lymph vessels, which agent contains one or more compounds from the group comprising 2,4,4-triphosphonobutyric acid, ethane-1,1,2,2-tetraphosphonic acid, propane-1,1,3,3-tetraphosphonic acid or butane-1,1,4,4-tetraphosphonic acid, optionally a tin(II) salt, and technetium-99m in physiologic saline. In the normal case, after labeling with technetium-99m, a patient receives an intraveneous injection of one tenth to one whole "small portion" of this type, which is called the labeling unit.

The advantages of the diagnostic agent based on the abovementioned triphosphonates or tetraphosphonates which is described here, compared with the phytate which is already known, are clear from the animal experiments detailed below:

Assuming that 2–20 mg of TPB, ETP, PTP or phytate are administered to humans, and assuming that the weight of human is 80 kg, this corresponds to an amount administered of 25–250 μg/kg of body weight. Calculating on the basis of the body weight of rats weighing 200 g, then administration of 5–50 μg of TPB, ETP, PTP or phytate per rat exactly reflects the relationships. Comparative investigations using amounts of this order have led to the data on organ distribution which are shown in the table.

The following conclusions can be drawn from the figures documented in the table:

With the substances, the accumulation in the liver decreases to some extent as the amount of substance is reduced, while the accumulation of activity in the kidneys, femur, blood and remainder of the body rises in parallel.

For all the amounts of substance investigated, the accumulation of ETP and TBP in the liver and spleen is markedly higher than that of phytate.

Likewise for all the amounts of substance investigated, the accumulation of activity with ETP, PTP and TPB in the kidneys, blood, femur and remainder of the body is clearly lower than with phytate.

Comparison of $^{99m}$Tc TPB, $^{99m}$Tc PTP and $^{99m}$Tc phytate after intravenous injection to dogs shows that:

The rates of elimination of the three products from the blood are comparable.

The decrease in activity via the liver after accumulation in the liver is complete is slower with TPB, ETP and PTP than with phytate. This is a particular advantage in certain circumstances in routine clinical investigations.

The excretion of activity with the urine is markedly less for TPB and PTP than for phytate; as much as 6.6% of the test dose of phytate, but only 0.05% of PTP and 0.6% of the test dose of TPB have been excreted 30 min. after injection.

TABLE

| | Organ distribution of $^{99m}$Tc TPB, $^{99m}$TC ETP and $^{99m}$Tc phytate in rats (n = 3) 30 minutes after injection as a function of the amount of substance administered (all data as a percentage of the amount of activity administered) | | | | | | | | | | | |
|---|---|---|---|---|---|---|---|---|---|---|---|---|
| Amount of substance | 50 μg | | | | 50 μg | | | | 50 μg | | | |
| Compound | TPB | ETP | PTP | phytate | TPB | ETP | PTP | phytate | TPB | ETP | PTP | phytate |
| Liver | 95.8 | 96.2 | 91.8 | 83.3 | 92.7 | 95.2 | 84.2 | 68.4 | 88.7 | 93.6 | 82.7 | 62.5 |
| Lung | 0.19 | 0.18 | 0.30 | 0.23 | 0.30 | 0.21 | 0.45 | 0.32 | 0.29 | 0.32 | 0.43 | 0.40 |

TABLE-continued

Organ distribution of $^{99m}$Tc TPB, $^{99m}$TC ETP and $^{99m}$Tc phytate in rats (n = 3) 30 minutes after injection as a function of the amount of substance administered (all data as a percentage of the amount of activity administered)

| Amount of substance Compound | 50 μg | | | | 50 μg | | | | 50 μg | | | |
|---|---|---|---|---|---|---|---|---|---|---|---|---|
| | TPB | ETP | PTP | phytate | TPB | ETP | PTP | phytate | TPB | ETP | PTP | phytate |
| Spleen | 1.30 | 2.10 | 1.31 | 0.60 | 0.88 | 2.13 | 1.23 | 0.38 | 0.99 | 1.30 | 1.10 | 0.25 |
| Kidneys | 0.12 | 0.12 | 0.16 | 1.74 | 0.37 | 0.16 | 0.37 | 2.81 | 0.39 | 0.26 | 0.38 | 2.97 |
| Femur/g | * | * | 0.052 | * | 0.29 | * | 0.088 | 0.74 | 0.30 | * | 0.089 | 1.09 |
| Thyroid | 0.03 | 0.03 | 0.05 | 0.04 | 0.03 | 0.03 | 0.04 | 0.03 | 0.03 | 0.04 | 0.05 | 0.03 |
| Blood/ml | 0.05 | 0.02 | 0.055 | 0.19 | 0.16 | 0.04 | 0.11 | 0.33 | 0.19 | 0.04 | 0.086 | 0.62 |
| Remainder of body | 5.6 | 7.8 | 9.3 | 22.1 | 11.5 | 11.2 | 16.0 | 29.7 | 12.6 | 10.4 | 18.4 | 36.1 |

*not determined

The clear deduction from these animal experiments is that $^{99m}$Tc ETP, $^{99m}$Tc PTP and $^{99m}$Tc TPB are unambiguously superior to $^{99m}$Tc phytate as a diagnostic agent for the visualization of RES-containing organs.

As already mentioned, the mechanism of accumulation of $^{99m}$TC ETP, $^{99m}$Tc PTP and $^{99m}$TC TPB is probably comparable to that of $^{99m}$Tc phytate. It is most probable that phytate forms colloids in the bloodstream with the calcium which is present there. Since the formation of particles in the blood greatly depends on the calcium status of the patient, on the rate of injection and on some other parameters which are difficult to define, it can be worthwhile to produce the colloid in vitro, for example by the addition of alkaline earth ions, such as calcium or barium ions. This colloid can then be prepared and labeled under exactly defined conditions and, by this means, the effect of the calcium status of the individual patient can be eliminated.

The use of small-particle colloids for lymphatic scintigraphy has been disclosed. At present, gold colloid ($^{198}$Au) and $^{99m}$Tc/Sb$_2$S$_7$ colloid are principally used for this. Because of its relatively poor radiation-physical properties, gold colloid is less suitable, and $^{99m}$Tc/Sb$_2$S$_7$ colloid resembles $^{99m}$Tc/sulfur colloid in being prepared by a comparatively elaborate process.

In order to check the utilizability of the new diagnostic agent for lymphatic scintigraphy, lymphatic scintigraphy using $^{99m}$Tc TPB was carried out on dogs. The deduction from the results of the experiments is that $^{99m}$Tc-TPB is also suitable for lymphatic scintigraphy.

EXAMPLE 1

Preparation of 2,4,4-triphosphonobutyric acid 105 g (0.365 mol) of tetraethyl methanediphosphonate are made alkaline with 33% strength sodium methylate solution. Then 86 g (0.365 mol) of ethyl 1-diethoxyphosphonoacrylate are added dropwise, with stirring at 40° C., over the course of 1 hour (the reaction is slightly exothermic) and the mixture is then stirred for 3.5 h. The reaction mixture is kept alkaline throughout the entire reaction time using sodium methylate solution. About 190 g of crude ethyl 2,4,4-tris(diethoxyphosphono)butyrate are obtained, the identity of which can be demonstrated by $^{31}$P NMR and which is hydrolyzed without further purification.

190 g of ethyl 2,4,4-tris(diethoxyphosphono)butyrate are dissolved in 600 ml of concentrated hydrochloric acid and stirred at 100° C. for 16 hours, hydrogen chloride being passed in at the same time. The reaction mixture is then evaporated to dryness, and the residue is dissolved in water and converted into the dipotassium salt using the appropriate amount of KOH. The dipotassium salt was recrystallized from aqueous methanol. 88.5 g (60% of theory) of the product are obtained.

| Elemental analysis (C$_4$H$_9$O$_{11}$P$_3$K$_2$): | | |
|---|---|---|
| | C | H | P |
| calculated: | 11.88% | 2.2% | 23.12% |
| found: | 12.0% | 2.1% | 22.5% |

The free acid can be obtained from the potassium salt.

EXAMPLE 2

400 mg of 2,4,4-triphosphonobutyric acid are dissolved in about 30 ml of double-distilled water. The pH of the solution, which is about 1.7 after this, is then adjusted to pH 6 using 1N NaOH. 8 mg of SnCl$_2$.2H$_2$O in 1 ml of 0.1N HCl are added to this solution, and the pH is again adjusted to 6 using 0.1N NaOH, and then the solution is made up to 40 ml. All the operations are carried out under a protective atmosphere of nitrogen gas. The solution thus obtained is frozen in individual 1 ml portions.

After 3 days, the solution is thawed and reacted with 1 ml of a $^{99m}$Tc-pertechnetate solution which contains 4.44 MBq (120 μCi) of $^{99m}$Tc. After 30 minutes, Sprague-Dawley rats weighing 200 g each receive 0.5 ml of this solution injected into the femoral vein. 3 animals are sacrificed with ether at 30 minutes and at 2 hours after the injection, and the organ distribution is determined. This results in the figures which follow (as percentage of the dose administered):

| | liver | spleen | kidneys | bone/g | urine | thyroid | blood/ml | remndr. of body |
|---|---|---|---|---|---|---|---|---|
| 30 min p.i. | 86.5 | 2.40 | 1.74 | 0.17 | 1.75 | 0.05 | 0.03 | 9.08 |
| 2 h p.i. | 88.3 | 3.06 | 1.12 | 0.22 | 2.02 | 0.04 | 0.01 | 8.27 |

EXAMPLE 3

8 g of sodium 2,4,4-triphosphonobutyrate are dissolved in about 60 ml of double-distilled water, the pH of the solution then being 8.5. After the pH had been adjusted to 7 with 1N HCl, 120 mg of SnCl$_2$.2H$_2$O in 3 ml of 1N HCl were added, the pH was adjusted to 6 using 0.1N NaOH, and the solution was made up to 160 ml with double-distilled water. All operations should be carried out under a protective atmosphere of nitrogen gas. The solution thus obtained is freeze-dried in individual 1 ml portions in snap-closure bottles which have previously been frozen with liquid nitrogen. The contents are covered with nitrogen and the bottles are closed.

After storage for some weeks, the lyophilizate is dissolved in 10 ml of physiologic saline containing 2 mCi of technetium-99m-pertechnetate. After 30 minutes, 3 Sprague-Dawley rats (about 200 g) each receive 0.1 ml of this solution injected into the femoral vein, and 30 minutes later the animals are sacrificed with ether and the distribution of activity over the organs is determined. The following mean figures (as percentage of the dose administered) result:

| liver | lungs | spleen | kidneys | thyroid | blood/ml | remndr. of body |
|---|---|---|---|---|---|---|
| 96.2 | 0.24 | 1.9 | 0.08 | 0.03 | 0.03 | 4.9 |

(The fact that the recovered activity totals 103.4% is because the figures are related to the dose administered and, in particular, because errors in measurement occur due to the inexact definition of the geometry of the organs, especially the remainder of the body.)

EXAMPLE 4

Labeling units are prepared as in Example 3, to which are added, between the addition of SnCl$_2$.2H$_2$O and making up to 160 ml, 160 mg of CaCl$_2$ in 10 ml of double-distilled water, whereupon the solution becomes cloudy. Animal experiments were carried out as described in Example 2, the following results being obtained (data as percentage of the dose administered):

| liver | lungs | spleen | kidneys | thyroid | blood/ml | remndr. of body |
|---|---|---|---|---|---|---|
| 94.3 | 0.25 | 2.16 | 0.08 | 0.01 | 0.03 | 4.2 |

EXAMPLE 5

1.40 g of ethane-1,1,2,2-tetraphosphonic acid are dissolved in about 20 ml of double-distilled water and the pH of the solution is adjusted to 7.0 using 1N sodium hydroxide solution. The total volume of this solution is adjusted to 100 ml with double-distilled water and, while excluding oxygen, 11 mg of SnCl$_2$.2H$_2$O in 5 ml of aqueous solution are added. The clear solution thus obtained is sterilized by filtration and filled, in 0.2 ml portions, into snap-closure bottles which have previously been cooled with liquid nitrogen, and is then freeze-dried. The contents are covered with nitrogen and the bottles are closed. A bottle then contains about 3.3 mg of Na salt of ETP (corresponding to about 2.7 mg of ETP) and about 11 µg of tin(II).

The substance is labeled with $^{99m}$Tc by the addition of 5 ml of physiologic saline which contains 1.5 mCi of technetium-99m-pertechnetate. After a reaction time of 15 minutes, three Sprague-Dawley rats each received 0.1 ml of this solution by intravenous injection. 30 minutes later, the animals were sacrificed and the organ distribution of $^{99m}$Tc ETP was measured. The following figures (as percentage of the dose administered) were found from this:

| liver | lungs | spleen | kidneys | thyroid | blood/ml | remndr. of body |
|---|---|---|---|---|---|---|
| 96.2 | 0.18 | 2.1 | 0.12 | 0.03 | 0.02 | 7.8 |

The total recovered activity of 104.5 percent is due, in particular, to errors in measurement of the remainder of the body and by the inexact definition of the geometry.

EXAMPLE 6

3.5 g of 1,1,3,3-propanetetraphosphonic acid (PTP) are dissolved in 250 ml of double-distilled water, and the solution is adjusted to pH 6 with 1N NaOH. 210 mg of SnCl$_2$.2H$_2$O, which are dissolved in 4.2 ml of 0.2N HCl, are added to this solution, and the pH is again adjusted to 6. The mixture is made up to 350 ml and individual 1 ml portions are prepared. (All the operations up to preparation of the individual portions are carried out under protective N$_2$ gas.) The contents are frozen and freeze-dried. One unit contains 10 mg of PTP and 0.6 mg of SnCl$_2$.2H$_2$O.

After storing for some weeks, the lyophilizate is dissolved in 10 ml of physiologic saline which contains 2 mCi of $^{99m}$Tc-pertechnetate. After 30 min, Sprague-Dawley rats (n=6) weighing about 200 g each receive 0.1 ml of this solution injected into the femoral vein. The animals are sacrificed with ether 30 min after injection, and the distribution of the activity over the organs is determined. The mean figures below result (as percentage of the dose administered):

| liver | lungs | spleen | kidneys | bladder + urine | thyroid | blood (1 ml) | bone | remndr. of body |
|---|---|---|---|---|---|---|---|---|
| 94.0 | 0.23 | 1.9 | 0.067 | 0.023 | 0.034 | 0.083 | 0.7 | 4.8 |

EXAMPLE 7

A labeling unit prepared as in Example 6 is made ready for injection with 5 ml of physiologic saline containing 10 mCi of $^{99m}$Tc-pertechnetate. 1 ml of this solution is injected into the ear vein of a dog (beagle) weighing 18 kg, and the change in activity with time over the abdominal cavity is followed using a gamma camera by the ROI technique. It emerges that the uptake of activity by the liver is complete after about 10 min. The lung and kidneys are not imaged.

The elimination from the blood and the renal excretion are also determined on the same animal. The clearance from the blood takes place in three phases with half-lives $t_1 = 3.25$ min (97%), $t_2 = 20.3$ min (2.4%) and $t_3 = 500$ min (0.6%). About 2.3% of the administered activity is excreted with the urine within the first 8 hours.

EXAMPLE 8

A TPB labeling unit which contained CaCl$_2$ as described in Example 4 was prepared with 5 ml of $^{99m}$Tc-pertechnetate solution which contained 5 mCi of $^{99m}$Tc per ml. Adult beagle dogs each received 0.3–0.4 ml of this solution injected subcutaneously into the hind paw. The change in the distribution of radioactivity with time over the hind legs was then followed using a gamma camera for 4 hours. The site of injection was shielded with lead in each case. It emerged from this that the radioactivity was transported away from the site of injection in the manner typical of lymph vessels, the lymph nodes being clearly visualized by a high accumulation of radioactivity. Thus it was demonstrated that the diagnostic agent according to the invention is also suitable for lymphatic scintigraphy.

We claim:

1. A diagnostic agent for the visualization of RES-containing organs and the lymph vessels, which contains one or more compounds labeled with technetium-99m selected from the group consisting of 2,4,4-triphosphonobutyric acid (TPB), ethane-1,1,2,2-tetraphosphonic acid (ETP), propane-1,1,3,3-tetraphosphonic acid (PTP) and butane-1,1,4,4-tetraphosphonic acid (BTP) or a suitable salt thereof in physiologic saline.

2. The diagnostic agent as claimed in claim 1, which additionally contains Ca ions.

* * * * *